US00PP29689P2

(12) United States Plant Patent
O'Connell

(10) Patent No.: US PP29,689 P2
(45) Date of Patent: Sep. 18, 2018

(54) ***KALANCHOE* 'ARUBA SUNRISE'**

(50) Latin Name: *Kalanchoe blossfeldiana*
Varietal Denomination: Aruba Sunrise

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/731,159

(22) Filed: Apr. 26, 2017

(51) Int. Cl.
*A01H 5/02* (2018.01)

(52) U.S. Cl.
USPC ..... Plt./339

(58) Field of Classification Search
USPC ..... Plt./339
See application file for complete search history.

(56) References Cited

PUBLICATIONS

PLUTO Plant Variety Database Mar. 1, 2018. p. 1.*

* cited by examiner

*Primary Examiner* — Annette H Para
(74) *Attorney, Agent, or Firm* — Cassandra Bright

(57) ABSTRACT

A new and distinct *Kalanchoe* cultivar named 'Aruba Sunrise' is disclosed, characterized by unique bi-color flowers of magenta-rose with feathery white aspices. Plants are robust, with an upright, uniform habit. Flowering is abundant and begins early. Foliage is olive green, with a bronze blush appearing under bright light conditions. *Kalanchoe* is a popular genus, typically produced for the floriculture industry, as well as for uses as container plants for the patio, or as landscape plants. The new variety is suitable for both indoor and outdoor ornamental uses.

2 Drawing Sheets

Latin name of the genus and species: *Kalanchoe blossfeldiana.*

Variety denomination: 'ARUBA SUNRISE'.

BACKGROUND OF THE INVENTION

The new cultivar is a product of a planned breeding program. The new variety originated from a cross pollination of the unpatented, proprietary seed parent, *Kalanchoe* 'Early Pink' with the pollen parent an unpatented, proprietary *Kalanchoe blossfeldiana* referred to as *Kalanchoe* 'Little Sun'. The cross pollination was made in September of 2013 in Vista, Calif., at a commercial greenhouse. The new cultivar 'Aruba Sunrise' was discovered by the inventor, Renee O' Connell in February of 2014 in Vista, Calif., at a commercial greenhouse.

Asexual reproduction of the new cultivar 'Aruba Sunrise' was first performed in Vista, Calif., at a commercial greenhouse, by terminal vegetative cuttings in April 2014. *Kalanchoe* 'Aruba Sunrise' has since produced multiple generations and has shown that the unique features of this cultivar are stable and reproduced true to type.

SUMMARY OF THE INVENTION

The cultivar 'Aruba Sunrise' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ARUBA SUNRISE'. These characteristics in combination distinguish 'ARUBA SUNRISE' as a new and distinct *Kalanchoe* cultivar:

1. *Kalanchoe* 'Aruba Sunrise' produces flowers that are bicolor, near magenta-rose, tipped by a rose-tinted white feathering at the apices, an unusual floral color combination for *Kalanchoe blossfeldiana.*
2. *Kalanchoe* 'Aruba Sunrise' is characterized by upright, uniform and robust growth.
3. *Kalanchoe* 'Aruba Sunrise' displays an early and freely flowering habit.
4. *Kalanchoe* 'Aruba Sunrise' is characterized by glossy, dark olive green leaves, displaying a bronze blush in bright light.

PARENTAL COMPARISON

Plants of the new cultivar 'Aruba Sunrise' are similar to the seed parent in most horticultural characteristics. However, plants of the new cultivar 'Aruba Sunrise' differ in the following:

1. 'Aruba Sunrise' exhibits more robust growth than 'Early Pink'.
2. 'Aruba Sunrise' produces bicolored flowers, whereas *Kalanchoe* 'Early Pink' has solid flowers.
3. 'Aruba Sunrise' has better postproduction longevity than 'Early Pink'.
4. 'Aruba Sunrise' displays a dark, glossy leaf texture as compared to the matte texture of the ovate leaf blade of *Kalanchoe* 'Early Pink'

Plants of the new cultivar 'Aruba Sunrise' are similar to the pollen parent in most horticultural characteristics. However, plants of the new cultivar 'Aruba Sunrise' differ in the following:

1. *Kalanchoe* 'Little Sun' produces small bicolored flowers, involving the colors of light yellow, salmon and white, whereas 'Aruba Sunrise' produces flowers that are magenta-rose, tipped by a rose-tinted white feathering at the apices.
2. 'Aruba Sunrise' produces more slender leaf blades than 'Little Sun'.
3. 'Aruba Sunrise' produces more branches than 'Little Sun'.
4. 'Aruba Sunrise' produces flowers that are somewhat larger than those of 'Little Sun'.

COMMERCIAL COMPARISON

The new cultivar 'Aruba Sunrise' can be compared to the patented commercial variety *Kalanchoe* 'Reese', U.S. Plant Pat. No. 21,521. Plants of the *Kalanchoe* 'Reese' are similar to plants of the new cultivar 'Aruba Sunrise' in most horticultural characteristics. However, the new cultivar 'Aruba Sunrise' differs in the following:

1. 'Aruba Sunrise' displays bicolor magenta-rose flowers with white feathering on the petal apices, whereas the flowers of *Kalanchoe* 'Reese' are orange in color.
2. 'Aruba Sunrise' produces leaves that are more narrow in width, often 3.5 cm wide at the widest point, versus those of *Kalanchoe* 'Reese', which can be 5.5 cm wide at the widest point.
3. 'Aruba Sunrise' expresses a copper bronze tint overlay on the green leaves, whereas *Kalanchoe* 'Reese' exhibits green leaves without the copper bronze tint.
4. Grown side by side, plants of 'Aruba Sunrise' had 7 offsets in a 13 cm pot, whereas 'Reese' had only 4 offsets.

The new cultivar 'Aruba Sunrise' can be compared to the unpatented commercial variety *Kalanchoe blossfeldiana* 'Drew'. Plants of *Kalanchoe* 'Drew' are similar to plants of the new cultivar 'Aruba Sunrise' in most horticultural characteristics. However, the new cultivar 'Aruba Sunrise' differs in the following:

1. 'Aruba Sunrise' displays bicolor magenta-rose flowers with white feathering on the petal apices, whereas the flowers of *Kalanchoe* 'Drew' are pink in color.
2. 'Aruba Sunrise' produces leaves that are more narrow in width, often 3.5 cm wide at the widest point, versus those of *Kalanchoe* 'Drew', which can be 7 cm wide at the widest point.
3. 'Aruba Sunrise' expresses a copper bronze tint overlay on the green leaves, whereas 'Drew' exhibits green leaves without the copper bronze tint.
4. Grown together, plants of 'Aruba Sunrise' had 7 offsets in a 13 cm pot, whereas plants of 'Drew' had only 3 offsets.

BRIEF DESCRIPTION OF THE PHOTOGRAPHS

The accompanying photographs in FIG. 1 and FIG. 2 illustrate in full color typical plants of 'ARUBA SUNRISE' grown in a commercial greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Kalanchoe* plant. The following photographs depict plants grown under natural light conditions of 3000-3500 foot-candles. Temperatures ranged from 3° C. to 39° C. night and day. No artificial light, photoperiodic treatments or chemical treatments were given to the plants.

DETAILED BOTANICAL DESCRIPTION

Figure 1:
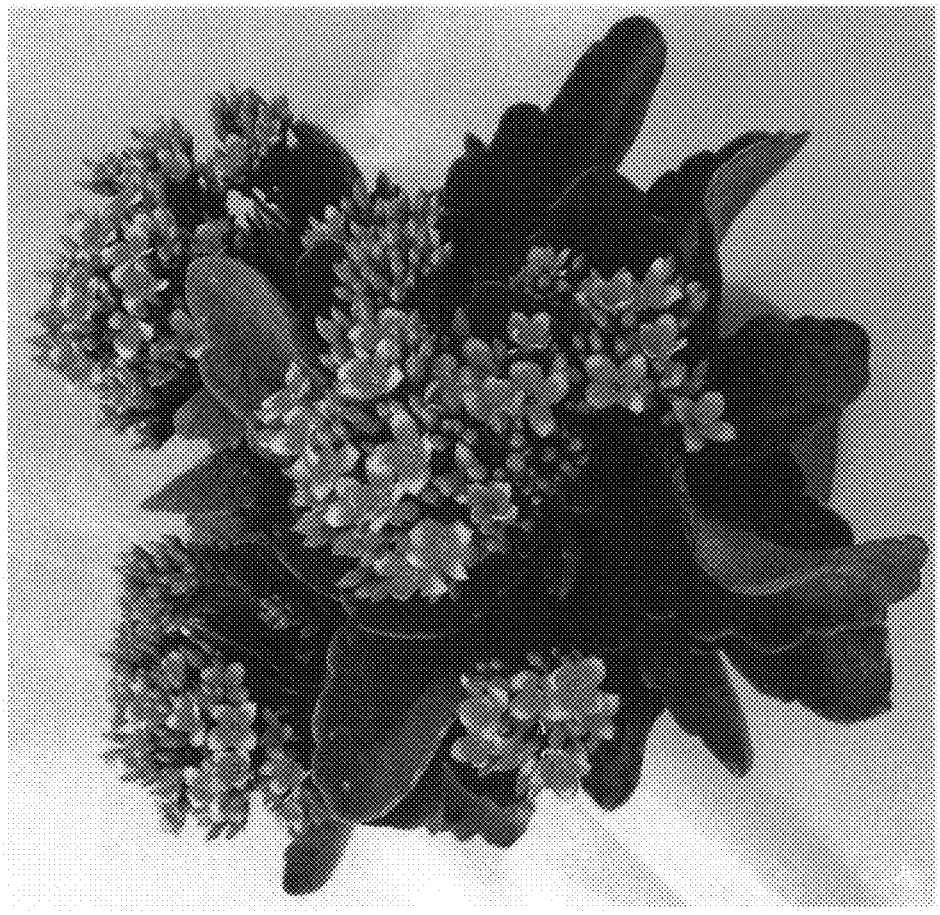
FIG. 1 illustrates in full color the side view of a typical plant of *Kalanchoe* 'Aruba Sunrise' grown in moderate light, with just a hint of bronze coloration.
Figure 2:
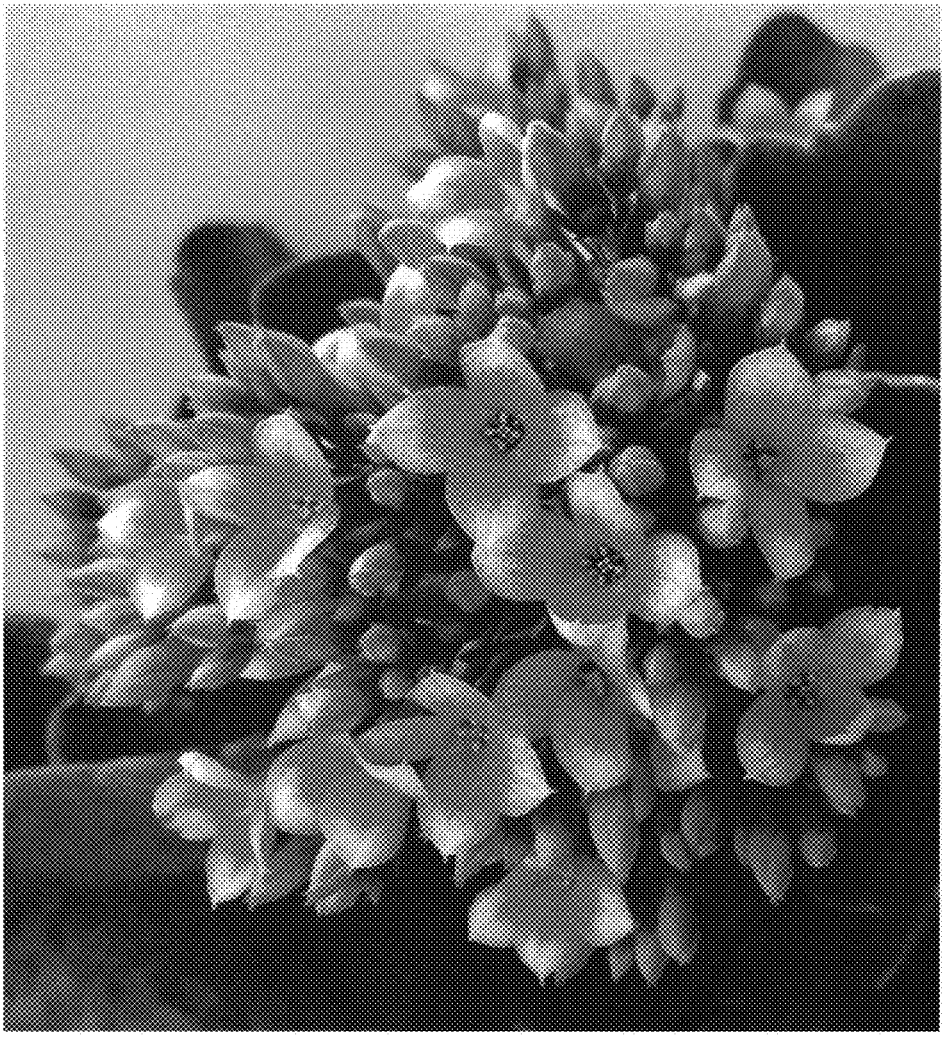
FIG. 2 illustrates in full color a close up of individual flowers and inflorescence of the new variety.

In the following description, color references are made to The Royal Horticultural Society Colour Chart, 2007 except where general terms of ordinary dictionary significance are used. The following observations and measurements describe 'Aruba Sunrise' plants in a commercial greenhouse in Vista, Calif. Temperatures ranged from 1° C. to 39° C. night and day. No artificial light, photoperiodic treatments or chemical treatments were given to the plants. Natural light conditions were approximately 3000 to 3500 fc of light. Measurements and numerical values represent averages of typical plant types.

Botanical classification: *Kalanchoe blossfeldiana* 'ARUBA SUNRISE'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 1 gallon.

Growth habit: Compact annual flowering succulent.

Height: Approximately 12 cm to top of highest leaf. Approximately 15 cm. to top of highest inflorescence.

Plant spread: Approximately 25 cm. Plant comprised of 3 rooted cuttings.

Growth rate: Moderately fast.

Branching characteristics: Central stem branches when pinched. Pinching occurs approximately 2 to 3 cm from Base. Central stem about 1.5 cm, colored near Yellow-Green 147A.

Length of primary lateral branches: About 2 to 5 cm.

Diameter of lateral branches: About 0.3 to 0.5 cm.

Quantity of primary lateral branches: Average 4 from a pinch.

Characteristics of primary lateral branches:

*Form*.—Round.

*Diameter*.—0.2 to 0.3 cm.

*Color*.—RHS Green 143C.

*Texture*.—Glabrous.

*Strength*.—Moderate, flexible.

Internode length: About 0.5 cm.

FOLIAGE

Leaf:

*Arrangement*.—Irregular, opposite.

*Average length*.—Average range 5.0 to 11.0 cm.

*Average width*.—5.0 cm, when flattened.

*Width at base*.—3.0 cm.

*Shape of blade*.—Ovate.

*Apex*.—Rounded.

*Base*.—Rounded and tapered.

*Margin*.—Deeply crenate, nearly lobed.

*Texture of top surface*.—Glabrous, glossy.

*Texture of bottom surface*.—Glabrous.

*Quantity of leaves per branch*.—Approximately 4 to 12.

*Color*.—Young foliage, upper side: Darker than Green 139A. Young foliage, under side: Near Yellow-Green 146A. Mature foliage, upper side: Darker than Green 139A, slightly tinted Greyed-Orange 175A. Mature foliage, under side, near apex: Yellow-Green 147A.

*Venation*.—There is no visual appearance of venation. Indistinguishable from leaf blade.

FLOWER

Natural flowering season: Flowering begins February or March, flowers last on plant at least 2 months in very good condition.

Inflorescence type and habit: Slightly flattened compound umbel.

Flower longevity on plant: Individual flowers, 2 to 3 weeks depending upon ambient temperatures.

Quantity of flowers per inflorescence: Average range 30 to 65. Larger terminal inflorescence with more flowers.

*Total inflorescence size*.—Height: Approximately 6 cm. Width: Approximately 8 cm.

*Corolla*.—Arrangement: 4-merous. Size: Length: Approximately 2.0 cm. Width: Approximately 1.2 cm at widest point. Lobe Length: Approximately 0.7 cm. Lobe Width: Approximately 0.6 cm. Tube Length: Approximately 0.9 cm. Tube Width: Approximately 0.3 cm.

*Petals*.—Margin: Entire. Shape: Spatulate. Apex: Mucronate. Texture: Glabrous all surfaces.

*Color*.—When opening: Petal color, inner surface: Near RHS Red-Purple N66B, streaky apical blotch near White N155C. Petal color, outer surface: Coloration divided at longitudinal mid-section: one side colored near Red-Purple 69B, one side colored near Red-Purple 63B. Fully opened: Petal color, inner surface: Near RHS Red-Purple N66A, streaky apical blotch near Red-Purple 69C. Petal color, outer surface: Coloration divided at longitudinal mid-section: one side colored near Red-Purple 69A, one side colored near Red-Purple 58C.

Bud: (Near opening):

*Shape*.—Narrow ovate.

*Length*.—Approximately 1.5 cm.

*Diameter*.—Approximately 0.3 cm.

*Color*.—Near RHS Greyed-Orange N170D flushed Greyed-Purple 186B.

Sepals:

*Quantity*.—5 fused at base.

*Margin*.—Entire.

*Shape*.—Narrow deltoid.

*Apex*.—Acute.

*Apex*.—Fused.

*Texture*.—Glabrous.

*Length*.—7 mm.

*Width*.—3 mm.

*Color*.—Outer: Near Green 143A. Mature sepals sometimes flushed Greyed-Purple N186D at apex. Inner: Near Green 143A.

Pedicels:

*Length*.—Approximately 0.3 cm.

*Width*.—Approximately 0.1 cm.

*Strength*.—Strong, flexible.

*Texture*.—Glabrous.

*Color*.—Near RHS Green 143A.

Fragrance: Slight musty scent.

REPRODUCTIVE ORGANS

Stamens: (Androecium).

*Number*.—Average 8.

*Filament length*.—Approximately 0.4 to 0.5 cm.

*Filament color*.—Near Yellow-Green 150D.

*Anther length*.—0.1 cm.

*Anther color*.—Near Yellow-Green 151D.

*Anther shape*.—Ovate-oblong.

*Pollen color*.—Near Yellow 2C, scant.

Pistil: (Gynoecium).

*Number*.—Average 4.

*Length*.—Approximately 0.9 cm.

*Style color*.—Near Yellow-Green 145A.

*Stigma*.—Shape: Rounded. Color: Near Yellow-Green N144B. Ovary Color: Near Yellow-Green 144B.

OTHER CHARACTERISTICS

Fruits and seeds: Typical to Genus. Minute, approximately 1 mm dry seeds. Colored brown, too small to accurately measure with color chart.

Temperature tolerance: Tolerates temperatures from approximately 0° C. to at least 32° C.

Disease/pest resistance: Neither resistance or susceptibility to normal diseases and pests of *Kalanchoe* has been observed.

Drought tolerance: Tolerates at least 2 weeks of high temperatures without supplemental water, showing no serious damage to plant.

What is claimed is:

1. A new and distinct cultivar of *Kalanchoe* plant named 'ARUBA SUNRISE' as herein illustrated and described.

* * * * *